(12) United States Patent
Porter

(10) Patent No.: US 9,119,938 B2
(45) Date of Patent: Sep. 1, 2015

(54) MEDICAL DEVICE WITH BI-COMPONENT POLYMER FIBER SLEEVE

(71) Applicants: Stryker Corporation, Kalamazoo, MI (US); STRYKER NV OPERATIONS LIMITED, Dublin (IE)

(72) Inventor: Stephen C. Porter, Piedmont, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 366 days.

(21) Appl. No.: 13/665,474

(22) Filed: Oct. 31, 2012

(65) Prior Publication Data

US 2013/0116659 A1    May 9, 2013

Related U.S. Application Data

(60) Provisional application No. 61/557,841, filed on Nov. 9, 2011.

(51) Int. Cl.
*A61M 25/00* (2006.01)
*A61L 29/08* (2006.01)

(52) U.S. Cl.
CPC .......... *A61M 25/0045* (2013.01); *A61L 29/085* (2013.01); *A61M 25/005* (2013.01); *A61M 25/0009* (2013.01); *A61M 25/0012* (2013.01); *A61M 2025/0046* (2013.01)

(58) Field of Classification Search
CPC .................. A61M 25/0012; A61M 25/0045; A61M 25/005
See application file for complete search history.

(56) References Cited

U.S. PATENT DOCUMENTS

| 2001/0010247 A1* | 8/2001 | Snow ........................... 156/171 |
| 2007/0060996 A1* | 3/2007 | Goodin et al. ............... 623/1.11 |
| 2009/0240235 A1* | 9/2009 | Murata .......................... 604/527 |

FOREIGN PATENT DOCUMENTS

| EP | 1 825 879 | 8/2007 |
| WO | 2006/113863 | 10/2006 |

OTHER PUBLICATIONS

PCT International Search Report and Written Opinion for PCT/US2012/062804, Applicant Stryker Corporation, Forms PCT/ISA/210, 220, and 237, mailed on Jan. 30, 2013 (9 pages).

* cited by examiner

*Primary Examiner* — Kevin C Sirmons
*Assistant Examiner* — Deanna K Hall
(74) *Attorney, Agent, or Firm* — Vista IP Law Group LLP

(57) ABSTRACT

An elongate medical device having a longitudinal axis and a surface; and a continuous, helical bi-component fiber wound around at least a portion of the surface of the medical device along its longitudinal axis, wherein the bi-component fiber has a cross-section with a generally flattened side and an inner core encased in a sheath, and wherein the inner core is aligned about the medical device.

14 Claims, 3 Drawing Sheets

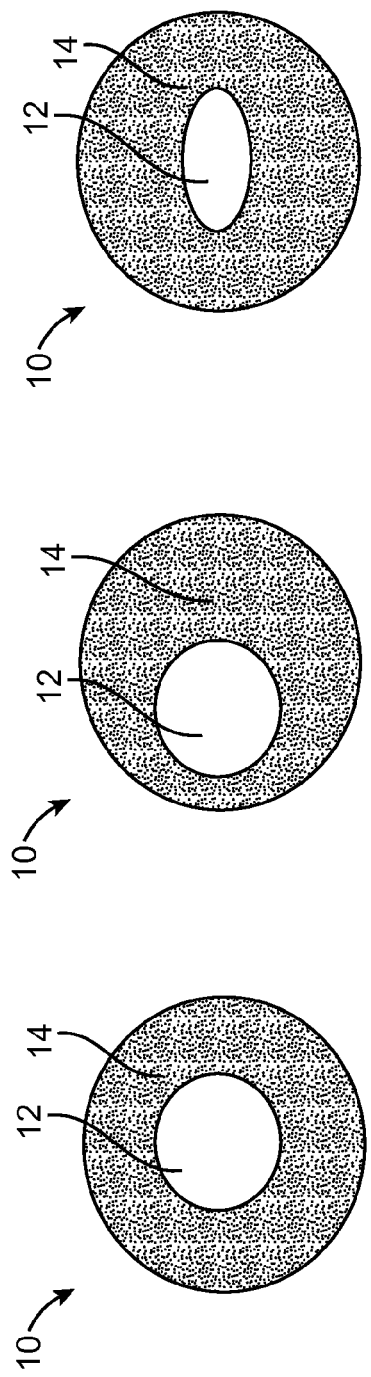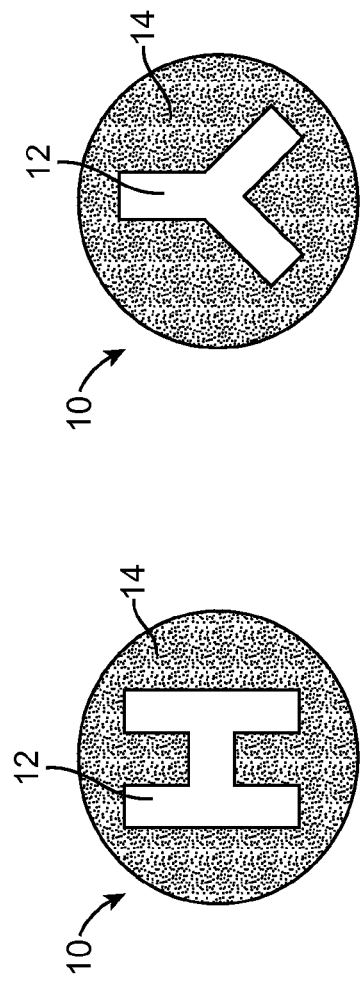

MEDICAL DEVICE WITH BI-COMPONENT POLYMER FIBER SLEEVE

RELATED APPLICATION DATA

The present application claims the benefit under 35 U.S.C. §119 to U.S. provisional patent application Ser. No. 61/557,841, filed Nov. 9, 2011. The foregoing application is hereby incorporated by reference into the present application in its entirety.

FIELD

The invention relates generally to medical devices coated with bi-component fibers.

BACKGROUND

The use of intravascular medical devices has become an effective method for treating many types of vascular disease. In general, a suitable intravascular medical device is inserted into the vascular system of the patient and navigated through the vasculature to a desired target site. Catheters and guidewires are often utilized to place intravascular medical devices such as stents and embolic devices at desired locations within the patient's body.

Intravascular catheters are currently utilized in a wide variety of minimally invasive medical procedures. Generally, an intravascular catheter enables a physician to remotely perform a medical procedure by inserting the catheter into the vascular system of the patient at a location that is easily accessible and thereafter navigating the catheter to the desired target site. By this method, virtually any target site in the patient's vascular system may be remotely accessed, including the coronary, cerebral, and peripheral vasculature.

Typically, the catheter enters the patient's vasculature at a convenient location such as a blood vessel in the neck or near the groin. Once the distal portion of the catheter has entered the patient's vascular system, the physician may urge the distal tip forward by applying longitudinal forces to the proximal portion of the catheter. For the catheter to effectively communicate these longitudinal forces, it is desirable for the catheter to have a high level of pushability and hoop strength, which confers kink and ovalization resistance.

Frequently, the path taken by a catheter through the vascular system is tortuous, requiring the catheter to change direction frequently. It may also be necessary for the catheter to double back on itself. Physicians often apply torsional forces to the proximal portion of the catheter to aid in steering the catheter. To facilitate the steering process, it is desirable that an intravascular catheter have a relatively high level of torqueability. Furthermore, in order for the catheter to conform to a patient's tortuous vascular system, it is desirable that intravascular catheters be very flexible.

The distance between the access site and the target site is often in excess of 100 cm. The inside diameter of the vasculature at the access site is often less than 5 mm. In light of the geometry of the patient's body, it is desirable to combine the features of torqueability, pushability, and flexibility into a catheter which is relatively long and has a relatively small diameter.

Ideally, the distal end of an intravascular catheter will be adapted to reduce the probability that the vascular tissue will be damaged as the catheter is progressed through the vascular system. This is sometimes accomplished by bonding or welding a relatively soft tip member to the distal end of an intravascular catheter.

After the intravascular catheter has been navigated through the patient's vascular system so that its distal end is adjacent the target site, the catheter may be used for various diagnostic and/or therapeutic purposes. One example of a diagnostic use for an intravascular catheter is the delivery of radiopaque contrast solution to enhance fluoroscopic visualization. In this application, the intravascular catheter provides a fluid path leading from a location outside the body to a desired location inside the body of a patient. In order to maintain a fluid path, it is desirable that intravascular catheters be sufficiently resistant to kinking and ovalization. These qualities can be secured through increased hoop strength. In addition, because such fluids are delivered under pressure, it is also desirable that intravascular catheters be sufficiently resistant to bursting or leaking.

One useful therapeutic application of intravascular catheters is the treatment of intracranial aneurysms in the brain. Approximately 25,000 intracranial aneurysms rupture each year in North America. An aneurysm which is likely to rupture, or one which has already ruptured, may be treated by delivering an embolic device or agent to the interior of the aneurysm. The embolic device or agent encourages the formation of a thrombus inside the aneurysm. The formation of a thrombus reduces the probability that an aneurysm will rupture. The formation of a thrombus also reduces the probability that a previously ruptured aneurysm will re-bleed. Thrombus agents which may be used include liquid thrombus agents such as cyanoacrylate, and granulated thrombus agents such as polyvinyl alcohol. An additional type of thrombus agent which is frequently used is a tiny coil. Any of the thrombus agents described above may be delivered using an intravascular catheter.

When treating an aneurysm with the aid of an intravascular catheter, the catheter tip is typically positioned proximate the aneurysm site. The thrombus agent is then urged through the lumen of the intravascular catheter and introduced into the aneurysm. Shortly after the thrombus agent is placed in the aneurysm, a thrombus forms in the aneurysm and is shortly thereafter complemented with a collagenous material which significantly lessens the potential for aneurysm rupture. It is desirable that the lumen of the catheter provides a path for delivering embolic devices to an aneurysm. To this end, it is desirable that the pathway through the catheter have a low friction surface.

The blood vessels in the brain frequently have an inside diameter of less than 3 mm. Accordingly, it is desirable that intravascular catheters intended for use in these blood vessels have an outside diameter which allows the catheter to be easily accommodated by the blood vessel. The path of the vasculature inside the brain is highly tortuous, and the blood vessels are relatively fragile. Accordingly, it is desirable that distal portion of a catheter for use in the brain be adapted to follow the highly torturous path of the neurological vasculature.

As described above, it is desirable to combine a number of performance features in an intravascular catheter. It is desirable that the catheter have a relatively high level of pushability and torqueability, particularly near its proximal end. It is also desirable that a catheter be relatively flexible, particularly near its distal end. The need for this combination of performance features is sometimes addressed by building a catheter which has two or more discrete tubular members having different performance characteristics. For example, a relatively flexible distal section may be bonded to a relatively rigid proximal section. When a catheter is formed from two or more discrete tubular members, it is necessary to form a bond between the distal end of one tubular member and the proximal end of another tubular member.

These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established. There are other ways of causing a catheter to proceed through the human vasculature to a selected site, but a guidewire-aided catheter is considered to be both quite quick and somewhat more accurate than the other procedures. Because guidewires navigate the same tortuous paths as intravascular catheters, it is also desirable that guidewires have relatively high levels of hoop strength, pushability, and torqueability.

SUMMARY

In accordance with one aspect of the disclosed inventions, a method of adding a layer to an elongate medical device is provided, the medical device having a longitudinal axis and an external surface, the method including (i) extruding a bi-component fiber having a cross-section with a generally flattened side, and comprising an inner core encased in an outer concentric sheath; (ii) winding the bi-component fiber helically around the medical device along its longitudinal axis with substantially closed pitch windings to thereby substantially cover at least a portion of its external surface; and (iii) fusing the windings of the wound bi-component fiber to each other and to the medical device to thereby form a substantially smooth and continuous layer around at least a portion of the medical device. By way of non-limiting example, the medical device may be a catheter. The method may optionally further include coating at least a portion of the wound and fused bi-component fiber and elongate medical device with a hydrophilic material. Also optionally, the method may include extruding a bi-component fiber having a cross-section with a generally flattened side, and comprising one or more cores each encased in a respective outer concentric sheath.

In one embodiment, winding the bi-component fiber helically around the medical device comprises interlocking adjacent windings of the bi-component fiber to each other.

In one embodiment, winding the bi-component fiber helically around the medical device aligns the inner core about the medical device. Optionally, winding the bi-component fiber helically around the medical device aligns the inner core axially, circumferentially, and/or radially about the medical device.

In one embodiment, the inner core has a four-sided cross-section, preferably a parallelogram.

In one embodiment, fusing the windings of the wound bi-component fiber comprises laminating the windings of the wound bi-component fiber.

In one embodiment, the inner core comprises a liquid crystal polymer.

In one embodiment, the bi-component fiber is a first bi-component fiber, the method further comprising: (iv) extruding a second bi-component fiber having a cross-section with a generally flattened side, and comprising an inner core encased in an outer concentric sheath; (v) after winding the first bi-component fiber helically around the medical device, winding the second bi-component fiber helically around the first bi-component fiber and medical device along the longitudinal axis of the medical device with substantially closed pitch windings to thereby substantially cover at least a portion of the first bi-component fiber and medical device; and (vi) fusing the windings of the wound second bi-component fiber to each other, to the windings of the wound first bi-component fiber, wherein winding the second bi-component fiber helically around the medical device aligns the inner core of the second bi-component fiber about the medical device. Optionally, winding the second bi-component fiber helically around the medical device aligns the inner core of the second bi-component fiber axially, circumferentially, and radially about the medical device. By way of non-limiting example, the first bi-component fiber is wound in a first axial direction and the second bi-component fiber is wound in an opposite axial direction to the first direction.

In accordance with a further aspect of the invention, an apparatus comprises an elongate medical device having a longitudinal axis and a surface, the device having a continuous, helical bi-component fiber wound around at least a portion of the surface along its longitudinal axis, wherein the bi-component fiber has a cross-section with a generally flattened side, and comprises an inner core encased in a sheath, and wherein the inner core is aligned about the medical device. Optionally, the inner core is axially, circumferentially, and radially aligned about the medical device. By way of non-limiting example, the medical device may be a catheter and the bi-component fiber forms a sleeve having a substantially smooth and continuous surface around at least a portion of the catheter.

In one embodiment, adjacent windings of the wound bi-component fiber are interlocked to each other.

In one embodiment, the inner core has a four-sided cross-section, preferably a parallelogram.

In one embodiment, the bi-component fiber is fused to form a continuous sleeve having a low void volume.

In one embodiment, the inner core comprises a liquid crystal polymer.

In one embodiment, the sheath comprises a low melt thermoplastic elastomer.

In one embodiment, the inner core has ribs projecting orthogonal to a longitudinal axis of the bi-component fiber, and wherein the ribs are aligned along the longitudinal axis of the medical device. Optionally, the ribs are aligned axially, circumferentially, and radially along the longitudinal axis of the medical device.

In one embodiment, the apparatus further comprises a hydrophilic material coating at least a portion of the wound and fused bi-component fiber and the elongate medical device.

In one embodiment, the bi-component fiber is a first bi-component fiber, the medical device further comprising a second bi-component fiber wound around at least a portion of the first bi-component fiber and medical device along the longitudinal axis of the medical device, wherein the second bi-component fiber has a cross-section with a generally flattened side, and comprises an inner core encased in a sheath, and wherein the inner core of the second bi-component fiber is aligned about the medical device. Optionally, the inner core of the second bi-component fiber is axially, circumferentially, and radially aligned about the medical device.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1A-E are axial cross-sectional views of sheath-core bi-component fibers according to various embodiments of the disclosed inventions.

DETAILED DESCRIPTION OF THE ILLUSTRATED EMBODIMENTS

Figure 2A:
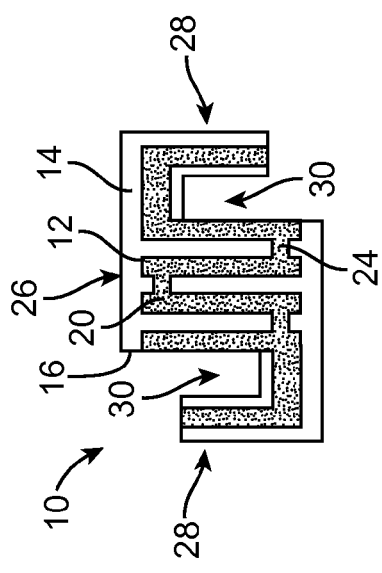
FIGS. 2A-E are axial cross-sectional views of sheath-core bi-component fibers according to other embodiments of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Bi-component fibers are typically formed by extruding two polymers of different chemical and/or physical properties from the same spinneret with both polymers contained within the same filament/fiber. "Co-spun fibers" are similar to, but not the same as bi-component fibers. A "co-spun fiber" is a group of filaments of different polymers spun from the same spinneret, but each filament is made of a single polymer. Bi-component fibers are also known as "conjugate fibers" in Asia.

Bi-component fibers exhibit capabilities not existing in either polymer alone. Bi-component fibers can be produced with any cross-sectional shape or geometry. Bi-component fibers are commonly classified by their fiber cross-section structures as sheath-core, side-by-side, islands-in-the-sea, and citrus fibers or segmented-pie cross-section types.

As shown in FIGS. 1A-E, sheath-core bi-component fibers 10 are those fibers where one of the components (the "core" 12) is fully surrounded by the second component (the "sheath" 14). This structure is employed when it is desirable for the surface to have the property of one of the polymers such as low melt temperature, while the core may contribute to strength. Sheath-core bi-component fibers 10 are further divided into concentric (FIGS. 1A, 1C, 1D, and 1E) and eccentric (FIG. 1B) fibers according to their axial cross-sectional profiles.

The core 12 may be made of materials with high tensile strength and higher melting temperature than the sheath material. Core materials include, but are not limited to, liquid crystal polymers (such as Vectra®), thermoset polymers (such as Ultem® PEI (polyetherimide)), thermoplastics, UHMWPE (ultra high molecular weight polyethylene), PEEK (polyether-ether-ketone), PLA (polylactic acid), PTT (polytrimethylene terephthalate), PPS (polyphenylene sulfide), PES (polyethersulfone), Surlyn® ionomer, POM (acetal), Halar® (ECTFE fluoropolymer), and non-polymer materials (such as metallic, ceramic, or carbon ribbons). When metallic, ceramic, carbon, or polymer ribbons are used as cores, the sheath is extruded over the ribbons. Alternatively, the metal, ceramic, carbon, or polymer fiber can be fragmented into small pieces, which are blended with the sheath polymer and linearly aligned and incorporated during extrusion.

The sheath 14 may be made of materials with a lower melting temperature relative to the core material. Sheath materials include, but are not limited to, low melt temperature thermoplastic materials, copolyester elastomers, HDPE (high density polyethylene), PP (polypropylene), PE/PP (polyethylene/polypropylene copolymer), polyurethanes, and nylons. Trade named sheath materials include Vestamid®, PEBAX®, Pellethane®, and other typical catheter shaft materials. Sheath materials may also include additives such as dyes and radiopacification agents such as powdered compounds of bismuth, barium, tantalum, etc.

Adhesion between the core 12 and the sheath 14 is not always essential for fiber 10 integrity. A highly contoured interface (FIGS. 1D, 1E, and 2A-D) between sheath and core can lead to mechanical interlocking between the core and the sheath that may be desirable in the absence of good adhesion.

The most common way of production of sheath-core bi-component fibers is a technique where two polymer liquids are separately directed to a position very close to the spinneret orifices and then extruded in sheath-core form. In the case of concentric fibers, the orifice supplying the core polymer is in the center of the spinning orifice outlet and flow conditions of core polymer fluid are strictly controlled to maintain the concentricity of both components when spinning. Eccentric fiber production is based on several approaches: eccentric positioning of the inner polymer channel and controlling of the supply rates of the two component polymers; introducing a varying element near the supply of the sheath component melt; introducing a stream of single component merging with concentric sheath-core component just before emerging from the orifice; and deformation of spun concentric fiber by passing it over a hot edge. Modifications in spinneret orifices enable one to obtain different shapes of core or/and sheath within a fiber cross-section. Important factors during spinning of these fibers include surface tensions, viscosities and flow rates of component melts.

Sheath-core bi-component fibers 10 are used as crimping fibers and bonding fibers. The sheath 14 of the fiber 10 is of a lower melting point than the core 12 and so in an elevated temperature, the sheath 14 melts, creating bonding points with adjacent fibers 10 and other adjacent surfaces. Bi-component fibers can also be tailored according to their intended use. If the product strength is the major concern, concentric bi-component fibers are used; if bulkiness is required at the expense of strength, as in some textile applications, the eccentric type of the fiber is used.

The sheath-core bi-component fibers 10 shown in FIGS. 2A and B have four-sided cross-sections. Further, the fibers 10, specifically the sheaths 14, have a generally rectangular cross-section with a pair of long sides 16 and a pair of short sides 18. Moreover, the cores 12 of the fibers 10 include ribs 20, which run substantially perpendicular to the long sides 16 and substantially parallel to the short sides 18.

In the embodiment in FIG. 2A, adjacent ribs 20 on the same core 12 connect to each other along a midline 22 bisecting the short sides 18 of the cross-section. The cross-sectional profile of this embodiment is formed by co-extruding the bi-component fibers 10 while controlling the shape of the core 12 and the sheath 14.

Figure 2B:
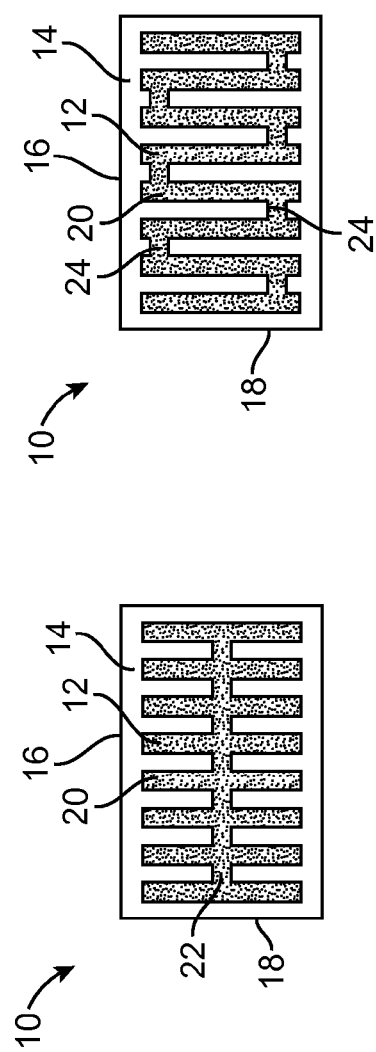

In the embodiment in FIG. 2B, adjacent ribs 20 on the same core 12 connect to each other adjacent respective ends 24 near the long sides 16 of the cross-section. Ribs 20 connect adjacent alternating ends 24. While ribs 20 in the embodiments shown in FIGS. 2A and 2B form regular patterns, any pattern of ribs 20 is within the scope of this disclosure. For instance, some ribs 20 from a fiber 10 may connect at a midline, which other ribs 20 connect adjacent ends 24. Also, ribs 20 do may connect to each other anywhere along their length.

Figure 2C:
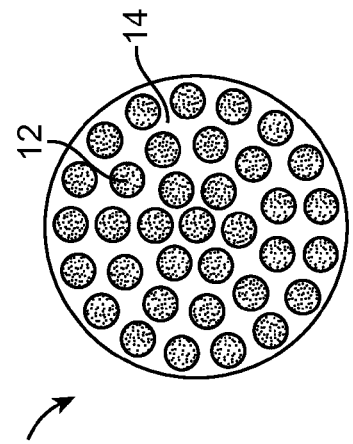
Figure 2D:
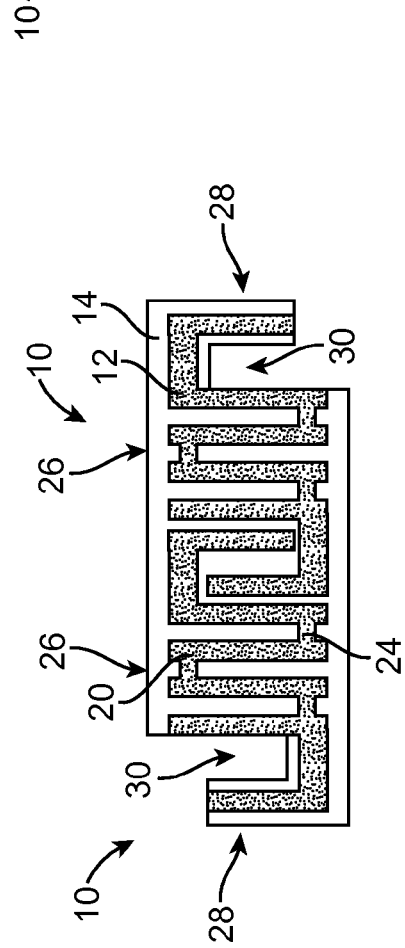

FIG. 2C depicts a sheath-core bi-component fiber 10 having an irregular cross-section including a substantially rectangular center portion 26 and two arms 28 extending from diagonally opposite corners of the center portion 26. The rectangular center portion 26 is similar in construction to the core 12 depicted in FIG. 2B. Each arm 28 and a long side 16 of the center portion 26 form an approximate "U" shape 30. The "U" shapes 30 formed by the two arms 28 of each cross-section point in opposite directions, such that when two lengths of fiber 10 are adjacent each other, the "U" shapes 30 can interlock, as shown in FIG. 2D.

Figure 2E:
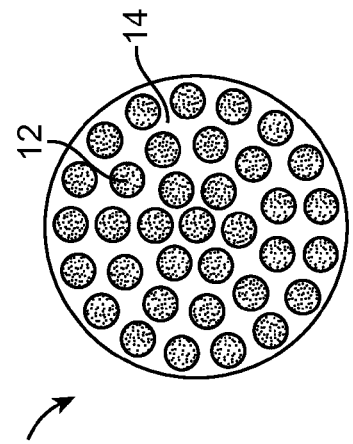

The fiber 10 shown in FIG. 2E has a circular cross section with a plurality of circular cores 12 in a circular sheath 14. Such sheath-core bi-component fibers 10 are also known as "islands-in-the-sea."

Figure 3:
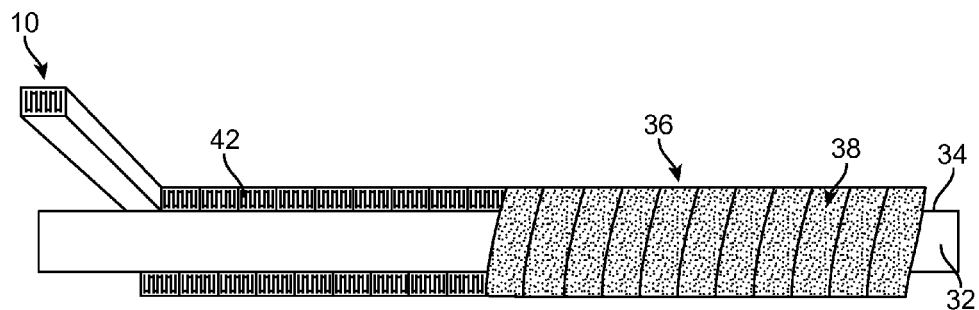
FIG. 3 is a side view of a coated medical device according to an embodiment of the disclosed inventions. Part of the sleeve has been cut away and the fiber is shown in cross-section for clarity.

As shown in FIG. 3, an elongate medical device 32 can be coated with a sleeve 36. The elongate medical device 32 can be a catheter, a guidewire, a sleeve, a tube, or any other elongate device that needs a high pressure rating, good pushability, good torque transmission, and/or kink resistance, while maintaining flexibility.

The sleeve 36 is formed by winding a sheath-core bi-component fiber 10 helically around the elongate medical device 32 along its longitudinal axis. The fiber 10 is wound with substantially closed pitch windings 38 to cover a portion of an exterior surface 34 of the elongate medical device 32 without leaving any substantial voids. Then the wound fiber 10 is heated to melt the sheath 14 and fuse the windings 38 to each other and to the exterior surface 34 of the elongate medical device 32, thereby eliminating substantially all voids.

Figure 4:
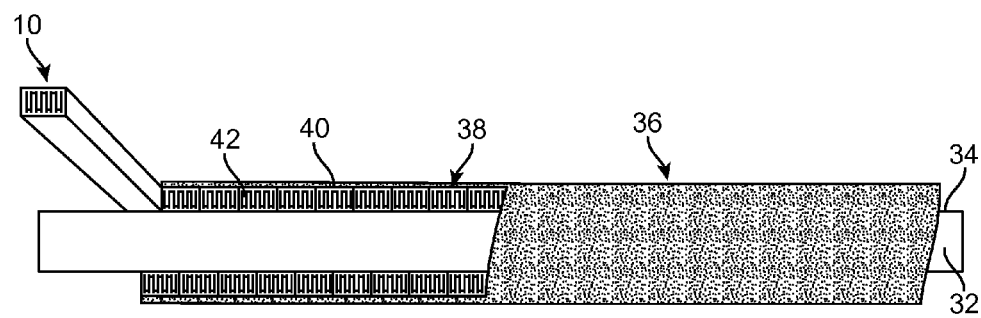
FIG. 4 is a side view of a coated medical device according to another embodiment of the disclosed inventions. Part of the sleeve has been cut away and the fibers are shown in cross-section for clarity.

In an alternative embodiment, shown in FIG. 4, a heat shrink tubing 40 with a higher melting temperature than the sheath 14 is loaded over the wound fiber 10 and the elongate medical device 32. Then heat is applied to shrink the heat shrink tubing 40 and melt the sheath 14 by slowly drawing a cylindrical heating zone over the device 32. As a result, the medical device 32 is coated with a sleeve 36 and a heat shrink tubing 40, which is typically removed after the sleeve 36 is formed. The medical device 32 can also be finally coated with a hydrophilic material.

Figure 5:
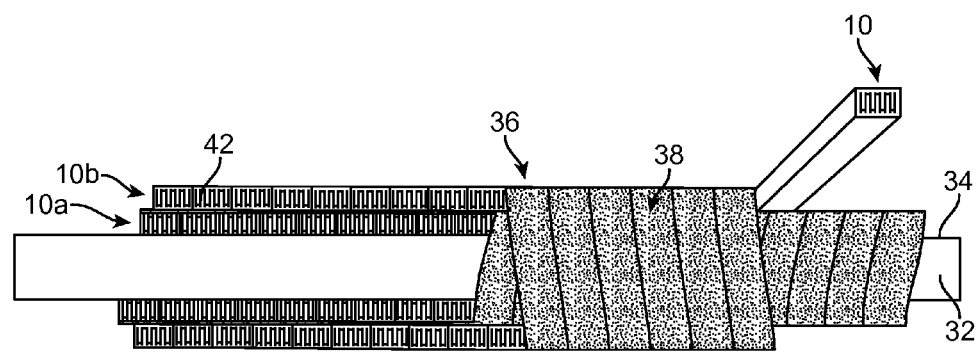
FIG. 5 is a side view of a coated medical device according to yet another embodiment of the disclosed inventions. Part of the sleeve has been cut away and the fibers are shown in cross-section for clarity.

The embodiment depicted in FIG. 5 is similar to the embodiment shown in FIG. 3. However, the sleeve 36 is formed by winding two sheath-core bi-component fibers 10a, 10b helically around the elongate medical device 32 along its longitudinal axis. The two sheath-core bi-component fibers 10a, 10b, may be different sections of a single sheath-core bi-component fiber 10. The two fibers are wound in opposite directions, and then melted and fused to each other and to the elongate medical device to form the sleeve 36.

As shown in FIGS. 3-5, the melted and fused windings 38 of the sheath-core bi-component fiber 10 form a substantially smooth and continuous sleeve 36 around the elongate medical device 32. The closed pitch of the windings 38 and melting of the sheath 14 ensures that the sleeve 36 is also substantially free of voids. For sheath-core bi-component fibers 10 like the one depicted in FIGS. 2C and 2D, adjacent windings 38 can interlock to improve mechanical coupling between windings 38 along the longitudinal axis of the medical device 32.

Preferably, the sheath-core bi-component fiber 10 has a non-round cross-section with at least one generally flattened side to align the fiber 10 and the core 12 radially during winding around the elongate medical device 32. More preferably, the cross section is a parallelogram (FIGS. 2A and 2B) or a construct comprised of multiple merged parallelograms (FIGS. 2c and 2d).

Helically winding the sheath-core bi-component fiber 10 around the elongate medical device 32, without rotating or twisting the fiber 10 about its own longitudinal axis, aligns the fiber 10 and the core 12 axially, circumferentially, and radially about the elongate medical device 32. Radial alignment is facilitated by the flat (vs. circular) surfaces of the fiber 10. When the core 12 is thus aligned, the ribs 20 form helices 42 around in the sleeve 36 around the elongate medical device 32. These helices 42 increase the hoop strength (kink and ovalization resistance), pushability, and torqueability of the medical device 32, while retaining flexibility.

In an alternative embodiment, the sleeve 36 is not disposed on the exterior surface 34 of the elongate medical device 32, but rather forms an axis-symmetric layer within the elongate medical device 32. After the sleeve 36 has been disposed around a core portion of the elongate medical device 32, other portions of the elongate medical device 32 may be disposed on or around the sleeve 36.

While the sheath-core bi-component fibers 10 in this disclosure each have one core 12, the claims encompass sheath-core bi-component fibers 10 having more than one core 12.

The above disclosure is intended to be illustrative and not exhaustive. This description will suggest many variations and alternatives to one of ordinary skill in this art. Further, the particular features presented in the dependent claims can be combined with each other in other manners within the scope of the invention such that the invention should be recognized as also specifically directed to other embodiments having any other possible combination of the features of the dependent claims.

What is claimed is:

1. A medical apparatus, comprising:
an elongate medical device having a longitudinal axis and a surface; and a continuous, helical bi-component fiber wound around at least a portion of the surface of the medical device along its longitudinal axis, wherein the bi-component fiber has a cross-section with a generally flattened side, and comprises an inner core encased in a sheath, and wherein the inner core is aligned about the medical device,
wherein the inner core comprises a plurality of ribs arranged in a pattern therein.

2. The medical apparatus of claim 1, wherein the inner core is axially, circumferentially, and radially aligned about the medical device.

3. The medical apparatus of claim 1, wherein inner core has a four-sided cross-section.

4. The medical apparatus of claim 1, wherein the bi-component fiber is fused to form a continuous sleeve having a low void volume.

5. The medical apparatus of claim 1, wherein the inner core comprises a liquid crystal polymer or a high melt thermoplastic elastomer.

6. The medical apparatus of claim 1, wherein the ribs project orthogonally to a longitudinal axis of the bi-component fiber, and wherein the ribs are aligned axially, circumferentially and radially along the longitudinal axis of the medical device.

7. The medical apparatus of claim 1, further comprising a hydrophilic material coating at least a portion of the wound and fused bi-component fiber and the elongate medical device.

8. The medical apparatus of claim 1, wherein the medical device comprises a catheter and the bi-component fiber forms a sleeve around at least a portion of the catheter, the sleeve having a substantially smooth and continuous surface.

9. The medical device of claim 1, wherein the bi-component fiber is a first bi-component fiber, the medical device further comprising a second bi-component fiber wound around at least a portion of the first bi-component fiber and medical device along the longitudinal axis of the medical device, wherein the second bi-component fiber has a cross-section with a generally flattened side, and comprises an inner core encased in a sheath, and wherein the inner core of the second bi-component fiber is aligned about the medical device.

10. The medical apparatus of claim 1, wherein adjacent windings of the wound bi-component fiber are interlocked to each other.

11. The medical apparatus of claim 1, wherein the sheath has a four-sided cross-section including two long sides and two short sides.

12. The medical apparatus of claim 11, wherein the ribs are disposed substantially perpendicular to the long sides, and substantially parallel to the short sides, of the sheath.

13. The medical apparatus of claim 1, wherein the ribs are connected to each other along a midline of each rib.

14. The medical apparatus of claim 1, wherein the ribs are connected to each other at alternating ends of each rib.

* * * * *